United States Patent [19]
Adams et al.

[11] Patent Number: 4,849,341
[45] Date of Patent: Jul. 18, 1989

[54] **DIAGNOSTIC TEST FOR *STAPHYLOCOCCAL MASTITIS* IN CATTLE**

[75] Inventors: D. Scott Adams; Irwin C. McGuire, Jr., both of Pullman, Wash.

[73] Assignee: ProScience Corporation, Sterling, Va.

[21] Appl. No.: 936,750

[22] Filed: Dec. 2, 1986

[51] Int. Cl.$^4$ ............... G01N 33/53; G01N 33/543; C12Q 1/14
[52] U.S. Cl. ............................ 435/7; 435/4; 435/29; 435/36; 435/820; 435/883; 436/501; 436/518; 436/811; 530/350; 530/825
[58] Field of Search ............... 435/4, 7, 29, 36, 820, 435/883; 436/501, 518, 811; 530/350, 825

[56] References Cited
U.S. PATENT DOCUMENTS
4,425,330 1/1984 Norcross et al. ............... 424/92

OTHER PUBLICATIONS
Davis A. et al., Journ Biol Chem., 252, No. 18:6544–6553, (1977).
Gudding, R., Acta Vet Scand., 21:242–255, (1980).

Primary Examiner—Esther M. Kepplinger
Assistant Examiner—Jack Spiegel
Attorney, Agent, or Firm—Iver P. Cooper

[57] ABSTRACT

The present invention relates to (1) an enzyme-linked immunosorbent assay (ELISA) for detection in milk of antibodies of any isotype which are specific for *Staphylococcus aureus* proteins in molecular weights ranging from 18,000 to 26,000 daltons, (2) a process for production and purification of said proteins, (3) a method of performing said ELISA utilizing said proteins and (4) use of said ELISA for detection of intramammary infection by *S. aureus*.

11 Claims, 6 Drawing Sheets

DIAGNOSTIC TEST FOR STAPHYLOCOCCAL MASTITIS IN CATTLE

BACKGROUND OF THE INVENTION

This invention relates to an S. aureus specific mastitis assay.

Bovine mastitis is an inflammation of the bovine mammary gland or udder. While mastitis is most often caused by Staphylococcus aureus, it is also attributable to many other organisms including Streptococcus agalactiae, Pseudomonas spp., certain coliform bacteria and mycoplasmas. Mastitis damages the udder and lowers milk production, and therefore imposes an economic burden on the dairy industry. In view of the complex etiology of mastitis, the optimum treatment course may not be apparent until the organism is identified. This is typically done commercially by culturing the organism and classifying it by conventional taxonomic procedures.

Staphylococcus aureus is extremely complex from an immunological standpoint, and a variety of staphylococcal antigens have been studied as potential reagents in immunoassays for staphylococcal antibodies in milk or sera. These include antibodies against protein A, see Live and Ranu, J. Bacteriol., 96:14-23 (1968); enterotoxins, see Fey, et al., J. Clin. Microbiol., 19:34-38 (1984); hemolysins, see Spencer, et al., Am. J. Vet. Res., 24:83-98 (1963); Surujballi and Fackrell, J. Clin. Microbiol., 19:394-98 (1984); Opdebeeck, et al., Am. J. Vet. Res., 43:1770-75 (1982); Christensson, et al., Acta Path. Microbiol. Immunol. Scand., Sec B, 91:351-56 (1983); crude capsular antigens, see Opdebeeck and Norcross, Am. J. Vet. Res., 46:1561 (1985); Watson and Davies, Res, Vet. Sci. 1985, 39:52-58; whole bacteria, see Mathison, et al., Am. J. Vet. Res., 45:2518-24 (1984); teichoic acid, see Granstrom., J. Am. Microbiol., 17:640-46 (1983); peptidoglycan, see Christensson, et al., J. Clin. Microbiol., 19:680-86 (1984); leukocidin, See Loeffler and Norcross, Am. J. Vet. Res., 46:1728 (1985); and nucleases, see Gudding, Acta. Vet. Scand., 21:1-14 (1980).

Norcross and Obdebeeck, U.S. Pat. No. 4,425,330, used Staphylococcus aureus strain Wood 46 to produce a staphylococcal alpha hemolysin, which they crudely purified by the method of Coulter, J. Bacteriol., 92:1655-62 (1966). This preparation was then used as an ELISA reagent.

Our invention is distinguished from that of Norcross and Obdebeeck by the fact that it uses highly purified antigens with a molecular weight range of 18,000 to 26,000 daltons. The significance of their use as antigens is that virtually all S. aureus infected cows have antibodies in their milk which bind them and uninfected cows do not. The antigen preparation contains no alpha or beta hemolytic activity or significant quantities of polysaccharide.

The only commercial product that serves the same purpose as our invention is bacterial culture, the disadvantages of which are as follows: (1) it detects only live bacteria and therefore antibiotic residues may interfere with detection, (2) it is often inaccurate because of contamination and therefore requires that a sterile sample be obtained, (3) it is labor intensive and time consuming and (4) it costs about 10 times as much per sample as the present invention. There if no commercial ELISA for detection of antibodies in milk for any purpose that we are aware of.

The molecular weights of some of the staphylococcal protein antigens are as follows: alpha hemolysin (36,000), beta hemolysin (33,000), gamma hemolysin (45,000) leucocidin (31,000), enterotoxin A (34,700); enterotoxin B (28,366), enterotoxin C (34,100), enterotoxin $C^2$ (34,000), enterotoxin E (29,600), enterotoxin F (20,000) and protein A (41,000). See Mollby, in Staphylococci and Staphylococcal Infections, at 644-645 (Easman and Adlam, eds: 1983), Vol. 2.

SUMMARY OF THE INVENTION

We have discovered that the 18-26KD fraction of Staphylococcus aureus exoproteins contains proteins which are bound by bovine milk antibodies from S. aureus-infected cows.

These proteins may conveniently be used in an enzyme-linked immunosorbent assay for detection of antibodies signifying intramammary infection by S. aureus, when present in milk.

With such an assay, it is possible to adopt an appropriate therapy for the infected cows, since the assay will not be positive if the mastitis is attributable to infection by, e.g., Streptococcus agalactiae or by Mycoplasma spp.

DETAILED DESCRIPTION OF THE INVENTION

Obtaining S. Aureus Exoproteins

Wood-46 of S. aureus obtained from the American Type Culture Collection ATCC 10832 is maintained frozen in broth or on blood agar base (Difco). Six-hundred microliters of an overnight culture (grown in CCY medium) of Wood-46 is added to 1 liter of CCY liquid medium consisting of 40 g casein hydrolysate, 10 g dialyzed yeast extract, 20 g Na beta glycerophosphate, 10 ml 50% Na lactate, 1 g $Na_2NPO_4$. $H_2O$, 0.4 g $KH_2PO_4$, 1 g$(NH_4)SO_4$, 80 mg dl-tryptophan, 100 mg l-cystine and q.s. to 1000ml with $dH_2O$. This is autoclaved together at 15 PSI for 30 minutes. To this is added 10 ml of a solution containing 20 mg thiamine and 40 mg nicotinic acid in 100 ml of $dH_2O$ (previously autoclaved separately). Ten ml of a solution of trace elements (also autoclaved separately) which contains 0.2 g $MgSO_4$. 7 $H_2O$, 0.1 g $MnSO_4$. 4 $H_2O$, 0.06 g $FeSO_4$. 7 $H_2O$ and 0.06 g citric acid in 100 ml of $dH_2O$ is also added to the large volume (Wooden, A. W., Biochemistry. J. 73: 225-237, 1959). The bacteria are grown under aerobic conditions for 24 to 48 hours either with shaking or by bubbling filtered air through the medium. Cultures are checked for purity by streaking on blood agar: tests for coagulase activity and latex agglutination (prothrombin/IgG coated), and a Gram's stain, are performed on the subculture. The cells are removed from the CCY medium by centrifugation at 1500 xg for 20 minutes and the supernatant is retained.

While Wood-46 is our preferred strain, other strains may be employed, particularly those considered likely to be the mastitis-causing agents in the region of interest. Among many other field strains, we compared exoproteins from an "alpha toxin" isolate and a "beta toxin" isolate with exoproteins of Wood 46 strain as antigens in our ELISA. Other media may be used, which may alter the relative production of the different exoproteins or which may simplify subsequent purification of the proteins from the medium.

Purification of the 18-26KD Exoproteins

Phenylmethylsulfonyl fluoride (0.13 M in acetone) to a final concentration of 1 mM and N-alpha-p-tosyl-1-lysine chloromethyl ketone as powder to a final concentration of 0.1 mM are added to the supernatant. The supernatant is dialyzed against a buffer of 50 mM TRIS pH 8.0 containing protease inhibitors, 0.01 mM phenylmethylsulfonyl fluoride, 0.001 mM N-alpha-p-tosyl-1-lysine chloromethyl ketone, 0.05 mM (ethylenedinitrilo)-tetraacetic acid (disodium salt) and 0.05 mM iodoacetamide and alternatively concentrated by evaporation in a fume hood through 5 to 6 changes of buffer until the volume inside the dialysis tubing (10 kd cutoff) is approximately 1/30th the original volume. The solution inside the tubing is then centrifuged for 30 minutes at 1500 xg and the supernatant is filtered through a 0.20 micron filter.

A protein assay (Bradford) is performed on the sample and 10 to 100 mg is placed on a Sephadex G-200 column equilibrated in 0.15 M phosphate buffered saline pH 7.5 containing the same concentration of protease inhibitors as listed above in the dialysis buffer. Four ml fractions are collected and the 77th through the 90th fractions which contain the antigen(s) of interest are pooled. This pool is placed inside dialysis tubing and concentrated by evaporation as before to approximately 4 ml.

Figure 1:
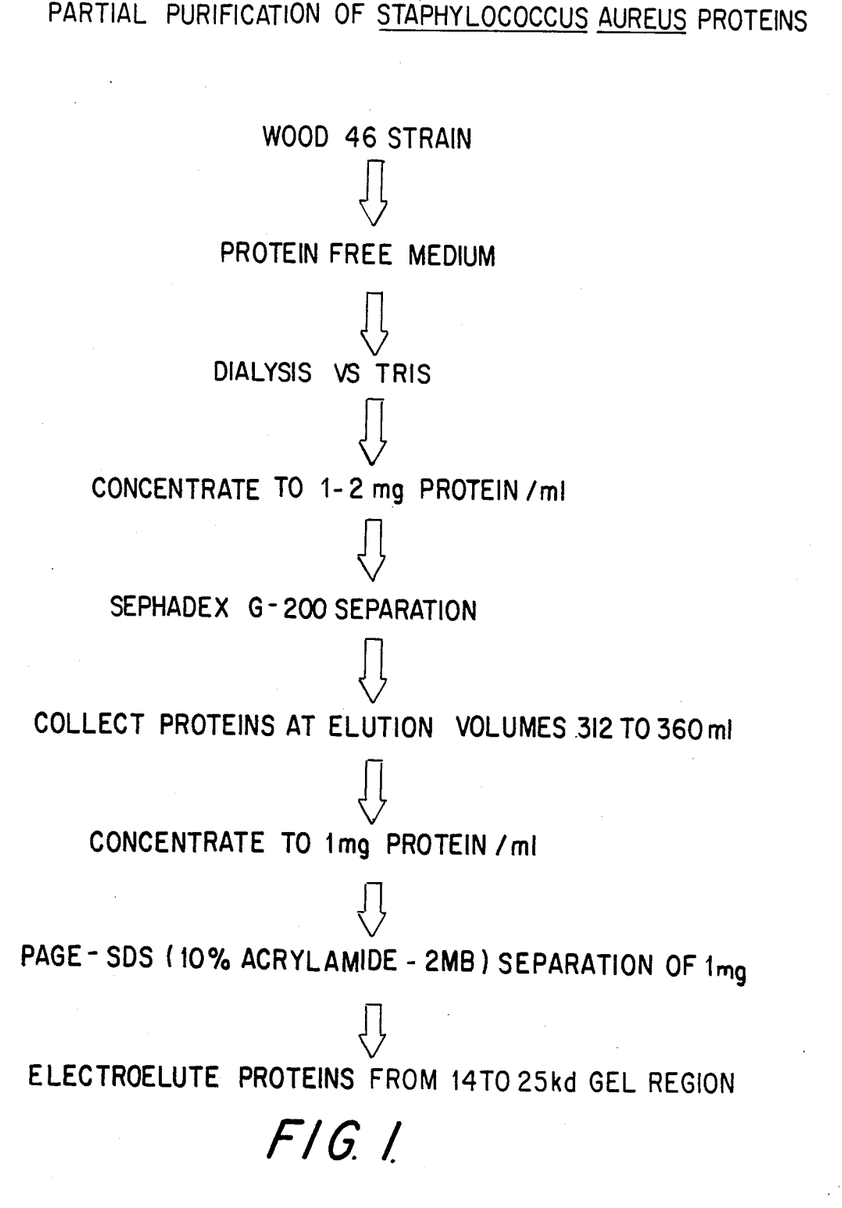
FIG. 1 shows the initial purification scheme employed to isolate 14-25KD exoproteins.
Figure 2:
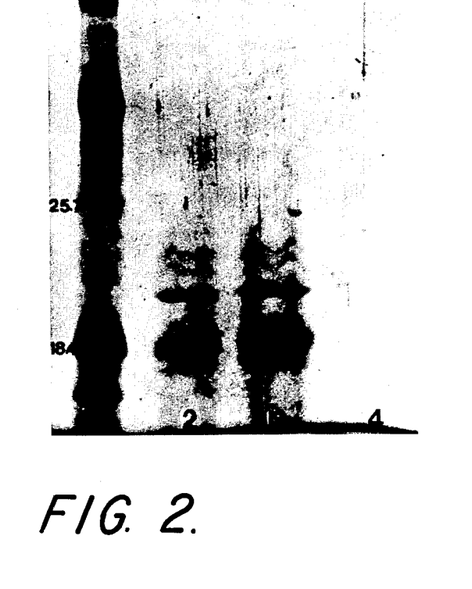
FIG. 2 is a silver stain of S. aureus exoproteins in a 12% polyacrylamide gel. Lane 1 was charged with a solution of standards; lane 2, with 25 ul of 10x concentrated ELISA antigen; lane 3, with 50 ul of 10x concentrated ELISA antigen; and lane 4, with 50 ul of unconcentrated ELISA antigen. Five or six bands are visible between 18 and 26KD.

This material is then subjected to polyacrylamide gel electrophoresis (PAGE): 15% polyacrylamide resolving gel, 5% stacking gel and 1% sodium dodecyl sulfate according to the method of Laemmli. The antigen solution is mixed with sample buffer containing 2-mercaptoethanol as a reducing agent and boiled. Remazol blue stained standard proteins are run simultaneously. The system is run at 130 v and 30 ma for approximately 6 hours. Approximately 4 major bands can be seen between the 25.7 and 18.4 kd standards when the sample lanes are stained with Coomassie blue. One or two additional bands can be seen in this region when the gel is stained with silver. (FIG. 2)

The region from the bottom of the 25.7 and the center of the 18.4 kd standard is cut from the gel, placed inside dialysis tubing with 15 ml of buffer and electrophoresed perpendicular to the long dimension of the gel at 30 v and 75 to 100 ma for 3 hours. The buffer in the tubing and the chamber is 25 mM TRIS pH 8.3 containing 0.192 M glycine.

After electroelution of the antigen from the gel the eluate is retained and used to coat polystyrene plates (Dynatech Immulon 1 or 2) for the ELISA that detects S. aureus infection specific antibody in milk samples. Dilution of the antigen is made in the electroelution buffer.

In the majority of the experiments in which we electroeluted 3 mm slices of the gel, the best signal-to-noise ratio was between 20 and 22 KD, though good ratios were obtained in the 20-24 KD range and at 18.4 KD.

Concentration of the antigen could be performed alternatively by ultrafiltration, polyethylene glycol concentration, ion exchange or salting out. If a monoclonal antibody, monospecific polyclonal antibodies or other specific binding ligand of high affinity could be produced (the antigens probably have enzyme activity and therefore substrate binding sites exist) the antigen(s) could be purified by immunoaffinity or ligand affinity chromatography directly from the supernatant.

We have found that our "active fraction" may have activity from 18 to 34 kd when DEAE is used to replace the G-200 column in the purification scheme. This spreading may be attributable to post translational modifications caused by proteolytic enzymes of S. aureus.

Comparison of 14-25 KD Fraction With Alpha and Beta Hemolysin Fractions as Immobilized Antigens for Use in Mastitis Antibody Assays Below are the initial screening results (optical densities) using purified exoproteins from the "beta toxin" isolate:

| S. aureus Infected | Coagulase Negative Infected | Uninfected |
|---|---|---|
| | Run 1 (anti $G_1$) | |
| 0.282 | 0.224 | 0.028 |
| 0.083 | 0.025 | 0.051 |
| 0.375 | 0.011 | 0.004 |
| 0.250 | 0.056 | 0.072 |
| | Run 2, anti $G_{1,2}$ | |
| 0.125 | 0.099 | 0.004 |
| 0.038 | 0.025 | 0.033 |
| 0.345 | 0.021 | −0.003 |
| 0.127 | 0.035 | 0.040 |
| | Run 3, Anti $G_2$ | |
| 0.342 | 0.031 | 0.008 |
| 0.197 | 0.026 | 0.015 |
| 0.348 | 0.019 | 0.004 |
| 0.035 | 0.028 | 0.007 |

Below are the initial screening results using purified exoproteins from the "alpha toxin" isolate.

| | Anti $G_2$ | |
|---|---|---|
| S. aureus Infected | Coagulase Negative Infected | Uninfected |
| 0.128 | 0.081 | 0.016 |
| 0.024 | 0.009 | 0.041 |
| 0.158 | 0.009 | 0.009 |
| 0.033 | 0.033 | 0.024 |

Below are screening results using purified exoproteins of Wood 46 isolate (Same day as the first table with "beta toxin".) The antigen was the only variable. All other conditions were identical.

| | Anti $G_1$ | |
|---|---|---|
| S. aureus Infected | Coagulase Negative Infected | Uninfected |
| 0.461 | 0.118 | 0.009 |
| 0.317 | 0.016 | 0.046 |
| 0.604 | 0.006 | 0.017 |
| 0.499 | 0.145 | 0.109 |

We reasoned at this point that since all of the infected cows had a good response and only some of the other cows had a moderate response that we could perhaps fractionate the antigen from Wood 46 in such a way as to keep the infection specific antigens and remove the non-specific components. The table below demonstrates the effect of the remainder of our purification process as described above.

| S. aureus Infected | Anti G$_1$ Coagulase Negative Infected | Uninfected |
| --- | --- | --- |
| 0.328 | 0.038 | −0.010 |
| 0.338 | 0.003 | 0.002 |
| 0.249 | −0.008 | −0.013 |
| 0.377 | 0.004 | −0.004 |

Selection and Testing of Milk for Mastitis-Related Antibodies

Our operating hypothesis was that cattle with intramammary infection by S. aureus secrete milk antibodies that can be detected by ELISA provided that the corrected antigen preparation is used.

In order to be assured that we would select antigen(s) of sufficient ubiquity among S. aureus populations to render our test sensitive and that we would select antigen(s) of sufficient uniqueness to render our test specific, we found it necessary to classify milk samples into two carefully defined categories: 1—samples from cows with intramammary S. aureus infection and 2—samples with no evidence of intramammary S. aureus infection.

To do this, somatic cell counts and bacterial cultures were performed on milk samples from Holstein diary cows on a monthly basis. The following summarizes our observations:

S. aureus was isolated from some cows on a single or just a few occasions and often without elevation of somatic cell counts. It became clear, as others have found (Dodd, F. H., National Mastitis Council Meeting, February, 1986), that merely isolating S. aureus from milk samples of cows without elevation of the somatic cell counts is insufficient evidence of intramammary infection. These isolations of S. aureus are apparently due to contaminations of samples from/by personnel and/or the environment or due to infections distal to the mammary gland itself. These were false positive samples.

S. aureus could be isolated from some cows only periodically but with somatic cell counts sometimes remaining elevated. This phenomenon is, perhaps, due to low grade infections by S. aureus in which the organism might be shed only periodically. Negative cultures of these cows were considered false negatives.

In addition, somatic cell counts were generally found to be elevated (greater than 150,000/ml) only in those cows with persistent and what was assumed to be intramammary infection. Somatic cell counts in cows without intramammary infection were generally less than 150,000/ml.

Based on these observations and for the purpose of screening antigen preparations the following definitions were applied to milk samples:

DEFINITION OF INTRA-MAMMARY INFECTION BY CULTURE: Milk samples must be contiguously culture positive for at least 4 months with a somatic cell count of greater than 150,000 cells/ml.

DEFINITION OF NON-INFECTION BY CULTURE: Milk samples from a cow must be culture negative for S. aureus during the lactation in which the sample being tested was taken and the somatic cell count must be less than 150,00 cells/ml.

We expected that formation of antibody to S. aureus would take some time and to insure that we would not be testing a sample from a cow that might spontaneously recovered from S. aureus infection before the next culture, milk samples from the first or last month a cow was cultured positive were not used for screening S. aureus antigens by ELISA.

Infection by coagulase negative staphylococci was defined as follows: four months or more contiguously culture positive. We did not use elevation of somatic cell counts as a criterion because these infections are usually distal to the mammary gland parenchyma and do not induce significant elevation of somatic cell counts. However, a few of the samples identified as coagulase negative staphylococci infected had elevated somatic cell counts which may have indicated an intramammary infection. Samples taken from the first or last month the cow was culture positive for coagulase negative staphylococci were not used for the ELISA screening.

ELISA ASSAY FOR MASTITIS-RELATED ANTIBODIES

In our ELISA, the test antigen was passively bound to a polystyrene plate, and exposed to the milk sample. The specific antibody in the milk binds to the antigen. Non-binding components are removed by washing and a horseradish peroxidase-labeled, isotype-specific anti-bovine Ig conjugate is added. A substrate is then provided to the peroxidase, resulting in a detectable product.

Dynatech Immulon 1 plates are coated with 0.05 ml of antigen for 3 hours at 37° C. and blocked by adding 0.05 ml PBS containing 0.2% azide and 0.5% bovine serum albumen for 2 hours at 37° C. The plates are then washed 3× with PBS containing 0.05% Tween 20. Milk samples are diluted 1:2 in PBS containing 0.02% azide, 0.5% BSA and 0.05% Tween and 20 and 0.05 ml is added to the wells. The plates are incubated for 30 minutes at 37° C. and then washed 4× with the same buffer as above. A 1:500 dilution of anti-bovine IgG$_{1,2}$ is diluted in PBS containing 0.5% BSA and 0.05% Tween 20 and 0.05 ml is added to each well to incubate for 30 minutes at 37C. After wasing 3× with wash buffer the substrate (5 amino-salicylic acid). The optical densities are determined spectorphotometrically at a wave length of 490 nm.

While HRPO is the preferred label, other labels known in the immunoassay art, including non-enzymatic labels, may be employed. The label may be directly attached to the anti-antibody, or an indirect means such as a biotin-avidin linkage may be used. The anti-antibody may be isotype-specific, merely bovine Ig-specific, or indeed Ig specific. An antibody-binding protein other than an antibody may be substituted for the anti-antibody. The assay format may be changed so that bound and unbound components are distinguishable without the need for physical separation.

Evaluation of 14–25 KD and 18–26 KD Exoprotein Fractions as Immobilized Antigens in Assay for Antibody on Larger Number of Samples Using the aforementioned criteria for infected and noninfected cattle, we tested 38 culture negative and 31 culture positive cows.

Statistics (ELISA O.D.)

Culture Negative Cows—Range=0.000 to 0.035; Mean=0.014; Standard Deviation=0.011

Culture Positive Cows—Range=0.089 to 0.634; Mean=0.332; Standard Deviation=0.123

Student's-t Statistic - The Fischer-Behrens test was used to compare the means because the variances differ significantly. $T_{cal}=14.38$ (P less than 0.001) with 30 degrees of freedom. $T_{0.05}=2.042$.

Figure 3:
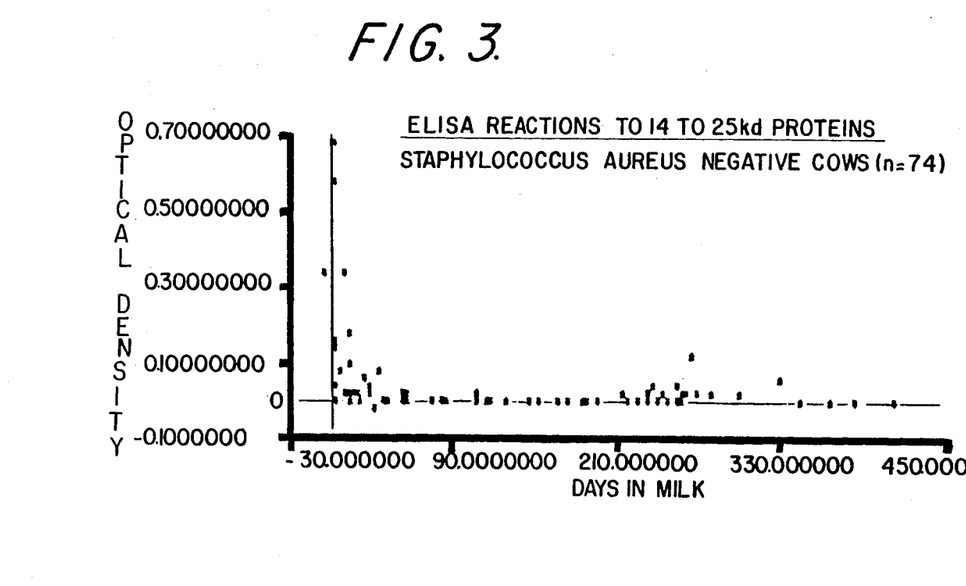
FIGS. 3-5 show the ELISA reactions of milk from (1) culture negative cows, (2) S. aureus positive cows, or (3) coagulase negative staph. Infected cows, respectively, to 14-25KD exoproteins.

FIG. 3 illustrates the ELISA reactions of culture negative cows plotted against Days in Milk. It can be seen that culture negative cows in the first 30 days of lactation often have antibody against these aligens in their milk. This is probably due to the fact that $IgG_1$ is actively transported from the serum to the milk during this period of time. The reactivity probably reprsents previous exposure to S. aureus but not active intramammary infection.

Thus, the ELISA reaction to the 14–25 KD proteins was, as desired, positive in S. aureus-infected cows, and negative in uninfected cows, or cows infected with coagulase negative organisms. Subsequent studies established that the critical (infection specific) antigens are in the 18–26 KD regions. Some 4 to 6 proteins are visible after Coomassie blue or silver staining of the gel; about the same after transblotting to nitrocellulose and staining with India ink.

Figure 4:
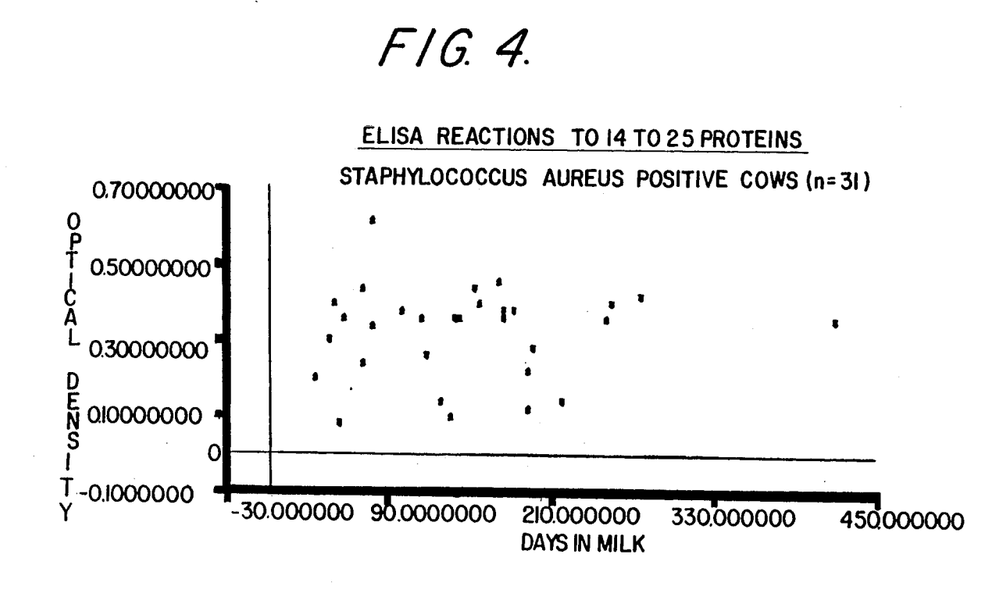

FIG. 4 shows the reactions of 31 culture positive cows that fit the definition described, with O.D. plotted against Days in Milk.

Figure 5:
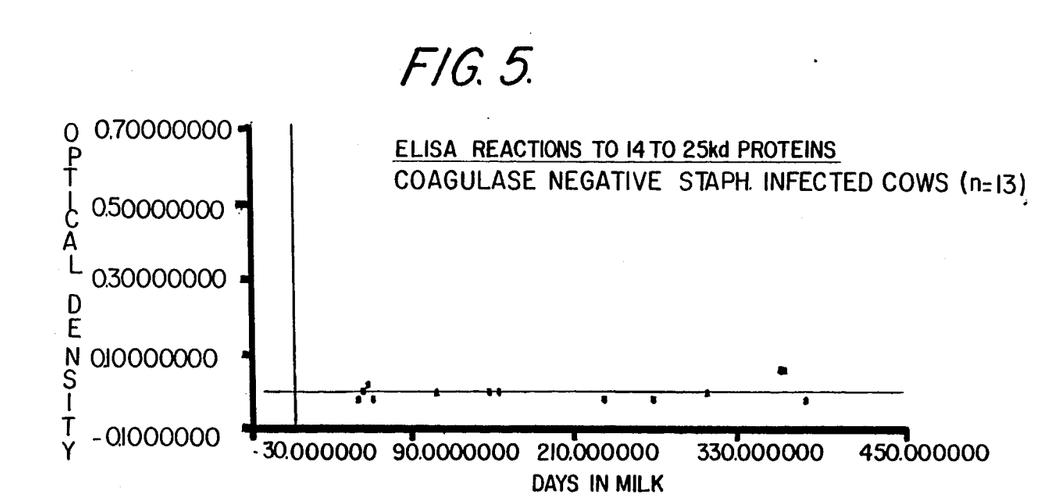

FIG. 5 shows the reactions of 13 coagulase negative staphylococcus species infected cows (4 months contiguous infection and sample not from first or last month). These cattle do not have detectable antibody against the S. aureus antigens in their milk.

Figure 6:
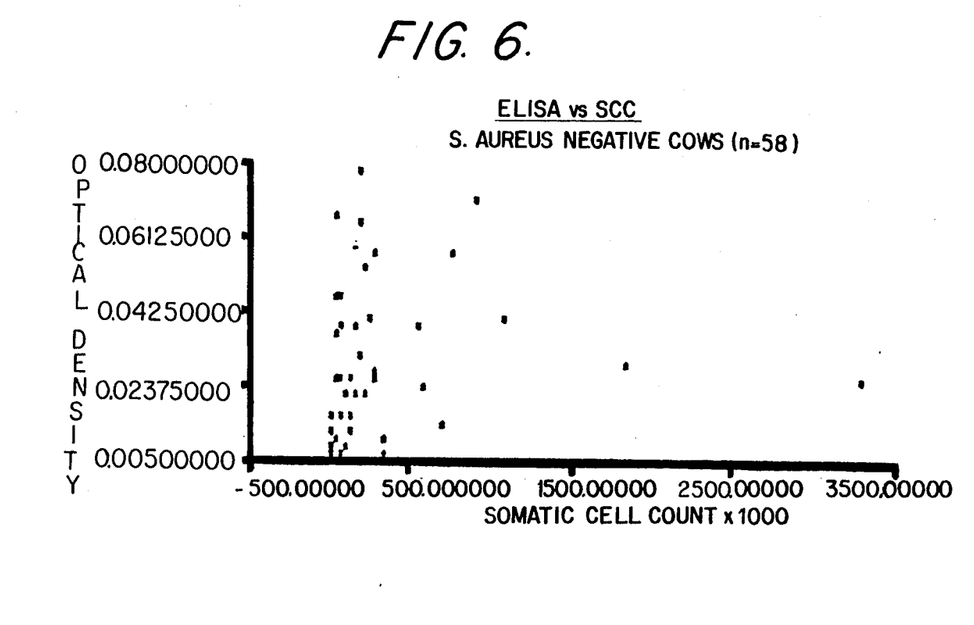
FIG. 6 shows that the reaction is not related to the somatic cell count.

Since most S. aureus infected cows have elevated somatic cell counts in their milk, we compared reactions of cows with elevated somatic cell counts (greater than 150,000) but not infected with S. aureus with their reactions in the ELISA. FIG. 6 shows the ELISA reaction plotted against the somatic cell count. Note that the O.D. scale is approximately 1/10th that of the other Figures. The correlation coefficient between these two variables is 0.177 (T=3.92, P less than 0.001). In other words, we are not somehow measuring somatic cell counts with our test.

In addition to the use of the aforementioned fractions as antigens, it is within the contemplation of this invention to purify individual proteins from these fractions and select those which appear to be infection-specific.

If it turns out that the antigens are subunits or breakdown products or larger molecules or if epitopes from the antigen(s) described herein could be identified, a "different" antigen preparation could be invented. With monoclonal antibody technology, anti-idiotype antibodies could be used to replace the antigen on the plate. A replica of the specific epitope(s) could be made by peptide synthesis or by expression of the DNA coding for the antigens in an expression vector.

These antigens may also have utility in a vaccine preparaton for S. aureus-infected cattle.

COMPARISON OF WOOD-46 AND "ALPHA TOXIN" STRAINS FOR 18 TO 26 KD ANTIGEN PRODUCTION

Both strains were grown under indentical conditions as described in the invention disclosure and concentrated exoproteins of each were tested for their ability to inhibit in the above described assay. As a rule the "alpha toxin" isolate produces 5 to 10 fold greater inhibition than Wood-46 strain on a per mg of protein basis.

While all of about 30 strains of S. aureus we have tested seem to produce inhibition, no strain other than "alpha toxin" has produced greater inhibition than Wood-46.

We have carried the exoprotein preparation from the "alpha toxin" strain through the antigen purification process and have found that the active fraction is also between 18 and 26 KD but tends to have greatest activity nearer 18 KD than Wood-46. It may be that the critical antigen(s) of "alpha toxin" are of slightly lower molecular weight than those of Wood-46. However due to the fact that they inhibit specific binding of antibody to the Wood-46 derived proteins we assume that the antigenic epitopes are substantially similar or identical.

We claim:

1. An immunological reagent comprising at least one non-nuclease antigen selected from the group consisting of the 20–24 KD Staphylococcus aureus exoproteins, and substantially free of antigens with molecular weights less than about 14 KD or greater than about 26 KD, said antigen being bound to a support.

2. The immunological reagent of claim 1, where the antigen is derived from the Wood-46 strain of Staphylococcus aureus.

3. The immunological reagent of claim 1, essentially free of alpha or beta hemolytic activity and essentially free of polysaccharide.

4. The reagent of claim 1 further comprising substantially all Staphylococcus aureus exoprotein antigens of a selected strain of Staphylococcus aureus which have molecular weights in the range of 20–24 KD.

5. The reagent of claim 4, wherein the selected strain is the Wood-46 strain.

6. The reagent of claim 4 further comprising substantially all Staphylococcus aureus exoprotein antigens of a selected strain of Staphylococcus aureus which have molecular weights in the range of 18–26 KD.

7. An immunological reagent comprising at least one staphylococcal mastitis infection-specific Staphylococcus aureus exoprotein which is not protein A, an enterotoxin, a hemolysin, teichoic acid, peptidoglycan, leukocidin or a nuclease, said reagent being substantially free of antigens with molecular weights less than about 14 KD or greater than about 34 KD, and said antigen being bound to a support.

8. A method of determining whether a cow of interest is suffering from mastitis caused by Staphylococcus aureus which comprises:
    (a) providing an immunological reagent according to claim 1;
    (b) incubating said reagent with a milk sample obtained from the cow of interest;
    (c) determining whether antibodies from said sample are bound to the antigens of said reagent; and
    (d) correlating the determination of step (c) to mastitis caused by Staphylococcus aureus.

9. The method of claim 8, further comprising detecting the bound antibodies by means of a labeled anti-antibody.

10. A method of determining whether a cow of interest is suffering from mastitis caused by Staphylococcus aureus which comprises:
    (a) providing an immunological reagent according to claim 4;
    (b) incubating said reagent with a milk sample obtained from the cow of interest;
    (c) determining whether antibodies from said sample are bound to the antigens of said reagent; and (d) correlating the determination of step (c) to mastitis caused by *Staphylococcus aureus*.

11. A method of determining whether a cow of interest is suffering from mastitis caused by *Staphylococcus aureus* which comprises:
(a) providing an immunological reagent according to claim 7;
(b) incubating said reagent with a milk sample obtained from the cow of interest;
(c) determining whether antibodies from said sample are bound to the antigens of said reagent; and
(d) correlating the determination of step (c) to mastitis caused by *Staphylococcus aureus*.

* * * * *

UNITED STATES PATENT AND TRADEMARK OFFICE
CERTIFICATE OF CORRECTION

PATENT NO. : 4,849,341
DATED : July 18, 1989
INVENTOR(S) : ADAMS et al.

It is certified that error appears in the above-identified patent and that said Letters Patent is hereby corrected as shown below:

ON TITLE PAGE:

Inventors: Delete "Irwin C. McGuire", insert therefor
-- Travis C. McGuire --

Signed and Sealed this

Twenty-second Day of October, 1991

Attest:

HARRY F. MANBECK, JR.

*Attesting Officer*   *Commissioner of Patents and Trademarks*